United States Patent
Sun et al.

(10) Patent No.: US 7,452,913 B2
(45) Date of Patent: Nov. 18, 2008

(54) POLYMORPHS OF PYRROLE SUBSTITUTED 2-INDOLINONE PROTEIN KINASE INHIBITORS

(75) Inventors: Changquan Sun, Portage, MI (US); Todd P. Foster, Kalamazoo, MI (US); Fusen Han, Eugene, OR (US); Michael Hawley, Kalamazoo, MI (US); Tom Thamann, Vicksburg, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 517 days.

(21) Appl. No.: 10/776,337

(22) Filed: Feb. 12, 2004

(65) Prior Publication Data

US 2004/0259929 A1 Dec. 23, 2004

Related U.S. Application Data

(60) Provisional application No. 60/448,863, filed on Feb. 24, 2003.

(51) Int. Cl.
*A61K 31/404* (2006.01)
*C07D 209/34* (2006.01)
(52) U.S. Cl. ...................... 514/414; 548/465
(58) Field of Classification Search ........... None
See application file for complete search history.

(56) References Cited

U.S. PATENT DOCUMENTS

| 6,333,333 | B1 * | 12/2001 | Bishop et al. ............. 514/290 |
| 6,339,100 | B1 | 1/2002 | Longley |
| 6,451,838 | B1 | 9/2002 | Moon et al. |
| 6,482,848 | B2 | 11/2002 | Moon et al. |
| 6,573,293 | B2 * | 6/2003 | Tang et al. ............... 514/414 |
| 6,710,067 | B2 | 3/2004 | Moon et al. |
| 2002/0010203 | A1 * | 1/2002 | Lipson et al. ............ 514/418 |
| 2003/0100555 | A1 | 5/2003 | Sun et al. |
| 2003/0130280 | A1 | 7/2003 | O'Farrell et al. |
| 2004/0063773 | A1 | 4/2004 | Tang et al. |

FOREIGN PATENT DOCUMENTS

WO WO01/60814 8/2001
WO WO02081466 10/2002

OTHER PUBLICATIONS

US pharmacopia #23, national formulary #18 (1995).*
Polymorphism in Pharmaceutical Solids, Brittain (1999).*
Rouhi, "The Right Stuff," Chem. & Engineering News (2003).*
C. A. London, "Kinase Inhibitors in the Treatment of Canine Cancer". Proceedings of Annual Canine Cancer Conference, 2002.
C. A. London, "Phase I Dose-Escalating Study of SU11654, a Small Molecule Receptor Tyrosin Kinase Inhibitor, in Dogs with Spontaneous Malignancies," Clinical Cancer Research, vol. 9, pp. 2755-2768, 2003.
Yongsheng Ma, et al., "Clustering of activating mutations in c-KIT's Juxtamembrane Coding Region in Canine Mast Cell Neoplasms," J Invest Dermatol 1999, pp. 165-170.
Yongsheng Ma, et al., "Indolinone Derivatives Inhibit Constitutively Activated KIT Mutants and Kill Neoplastic Mast Cells," J Invest Dermatol 2000, pp. 392-394.
N.K Pryer et al, "Proof of Target for SU11654: Inhibition of KIT Phosphorylation in Canine Mast Cell Tumors", Clinical Cancer Research, vol. 9, pp. 5729-5734, 2003.

* cited by examiner

*Primary Examiner*—Kamal Saeed
*Assistant Examiner*—Michael P Barker
(74) *Attorney, Agent, or Firm*—Timothy J. Gumbleton

(57) ABSTRACT

The present invention relates to polymorphs of the 3-pyrrole substituted 2-indolinone compound 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide.

16 Claims, 3 Drawing Sheets

POLYMORPHS OF PYRROLE SUBSTITUTED 2-INDOLINONE PROTEIN KINASE INHIBITORS

CROSS-REFERENCE

This application claims priority under 35 U.S.C. 119(e) to U.S. Provisional application Ser. No. 60/448,863 filed on Feb. 24, 2003, the disclosure of which is incorporated herein by reference in its entirety.

BACKGROUND OF THE INVENTION

1. Field of Invention

The present invention relates to polymorphs of the 3-pyrrole substituted 2-indolinone compound 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide.

2. State of the Art 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide is a compound that exhibits protein kinase (PK) modulating ability. The compound is therefore useful in treating disorders related to abnormal PK activity.

Briefly, PKs are enzymes that catalyze the phosphorylation of hydroxy groups on tyrosine, serine and threonine residues of proteins. The consequences of this seemingly simple activity are staggering, since virtually all aspects of cell life (e.g., cell growth, differentiation and proliferation) and, in one way or another, depend on PK activity. Furthermore, abnormal PK activity has been related to a host of disorders, ranging from relatively non-life threatening diseases such as psoriasis to extremely virulent diseases such as glioblastoma (brain cancer).

5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide is an inhibitor of receptor tyrosine kinases (RTKs); a class of PK. The RTKs and their ligands, VEGF, PDGF, and FGF mediate neo-vascularization, known as angiogenesis, in solid tumors. Consequently, by inhibiting the RTKs, the growth of new blood vessels into tumors may be inhibited. Theoretically, this new class of molecules, termed antiangiogenesis agents, have much less toxicity to the body compared to conventional anti-cancer drugs. 5-[5-fluoro-2-oxo-1,2-dihydroindol-(3Z)-ylidenmethyl]-2,4-dimethyl-1H-pyrrole-3-carboxylic acid (2-pyrrolidin-1-yl-ethyl)-amide is currently being developed for treating cancers in companion animals, mainly dogs and is also useful for the treatment of, inter alia, cancer in humans. Such cancers include, but are not limited to leukemia, brain cancer, non-small cell lung cancer, squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal stromal cancer. Also, overexpression of mast cells, including, but not limited to, mastocyctosis is contemplated.

SUMMARY OF THE INVENTION

The inventors have found that the compound 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide exists in two polymorphic forms, polymorph I and polymorph II, each having distinctly different physical properties.

In a first embodiment, therefore, the invention relates to a compound of the formula I:

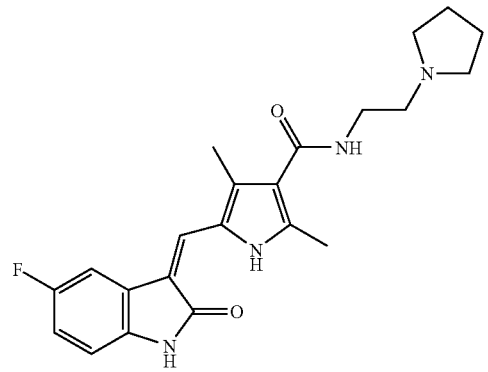

substantially free of the polymorph I form.

In a second embodiment, the invention relates to a compound of the formula I:

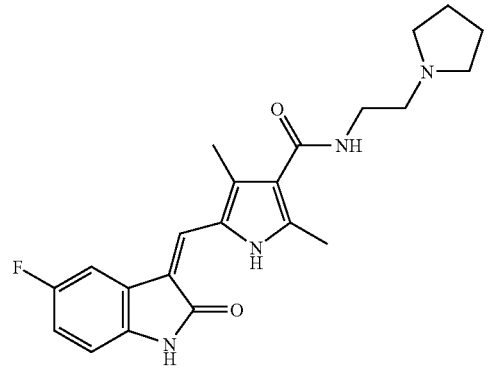

substantially free from the polymorph II form.

In a preferred embodiment, the compound of the first embodiment has the PXRD pattern shown in FIG. 1, form II and the compound of the second embodiment has the PXRD pattern shown in FIG. 1, form I.

In a third embodiment, the invention relates to a composition comprising polymorph I of a compound of formula I:

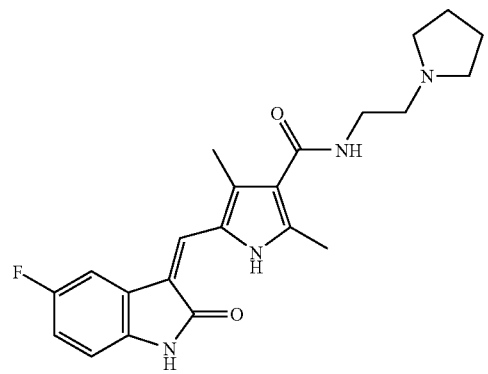

wherein polymorph I comprises more than about 85 weight percent of the composition; or more than about 90 weight percent of the composition; or more than about 95 weight percent of the composition; or more than about 99 weight percent of the composition.

In a fourth embodiment, the invention relates to a composition comprising polymorph II of a compound of formula I:

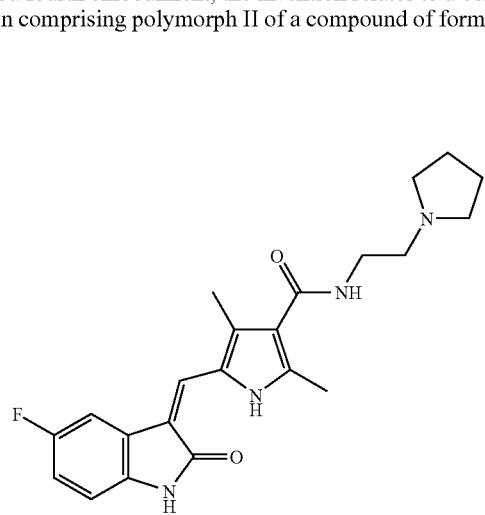

wherein polymorph II comprises more than about 85 weight percent of the composition; or more than about 90 weight percent of the composition; or more than about 95 weight percent of the composition; or more than about 99 weight percent of the composition.

In a fifth embodiment, the invention relates to a polymorph of the compound of the formula I:

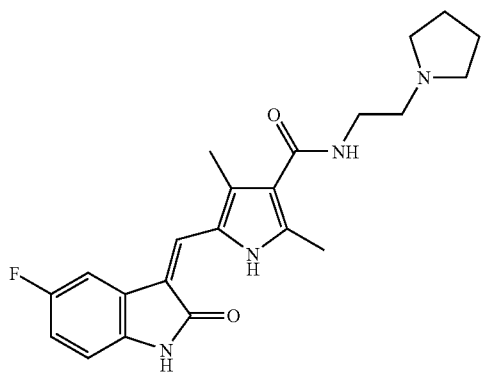

wherein said polymorph is made by:
(a) dissolving said compound in an acidic aqueous solution;
(b) basifying said aqueous solution thereby precipitating said compound substantially free from the polymorph II form; and
(c) isolating the precipitated polymorph I form of said compound.

In a sixth embodiment, the invention relates to a polymorph of the compound of the formula I:

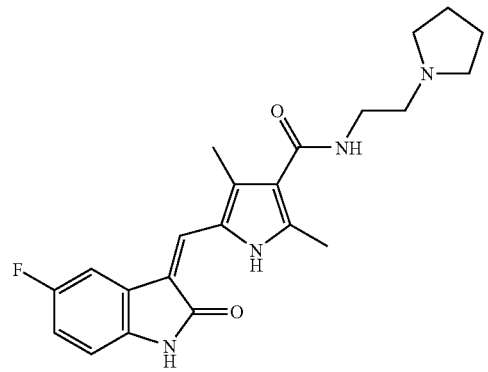

wherein said polymorph is made by:
(a) dissolving said compound in a polar organic solvent that does not form hydrogen bonds;
(b) evaporating said polar organic solvent thereby precipitating said compound substantially free from the polymorph II form; and
(c) isolating the precipitated polymorph I form of said compound.

In a seventh embodiment, the invention relates to a polymorph of the compound of the formula I:

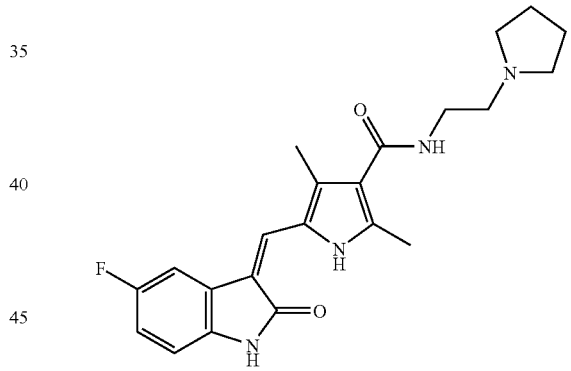

wherein said polymorph is made by:
(a) dissolving said compound in a polar organic solvent that forms hydrogen bonds;
(b) evaporating said polar organic solvent thereby precipitating said compound substantially free from the polymorph I form; and
(c) isolating the precipitated polymorph II form of said compound.

In a preferred embodiment of the present invention, the polar organic solvent of the sixth embodiment that does not form hydrogen bonds is THF. In another preferred embodiment, the polar organic solvent of the seventh embodiment that forms hydrogen bonds is methanol.

In an eighth embodiment, the invention relates to a pharmaceutical composition comprising a compound of first or second embodiments and a pharmaceutically acceptable carrier or excipient.

In a ninth embodiment, the invention relates to a method for the modulation of the catalytic activity of a protein kinase comprising contacting said protein kinase with a compound of the first or second embodiments. In a preferred embodiment, the protein kinase is selected from the group consisting of a receptor tyrosine kinase, a non-receptor tyrosine kinase and a serine-threonine kinase.

In an tenth embodiment, the invention relates to a method for treating or preventing a protein kinase related disorder in an organism comprising administering a therapeutically effective amount of a pharmaceutical composition comprising a compound of the first or second embodiments and, a pharmaceutically acceptable carrier or excipient to the organism. In a preferred embodiment, the protein kinase related disorder is selected from the group consisting of a receptor tyrosine kinase related disorder, a non-receptor tyrosine kinase related disorder and a serine-threonine kinase related disorder. In another preferred embodiment, the protein kinase related disorder is selected from the group consisting of an EGFR related disorder, a PDGFR related disorder, an IGFR related disorder, a c-kit related disorder and a flk related disorder. In yet another preferred embodiment, the protein kinase related disorder is a cancer selected from the group consisting of leukemia, brain cancer, non-small cell lung cancer, squamous cell carcinoma, astrocytoma, Kaposi's sarcoma, glioblastoma, lung cancer, bladder cancer, head cancer, neck cancer, melanoma, ovarian cancer, prostate cancer, breast cancer, small-cell lung cancer, glioma, colorectal cancer, genitourinary cancer and gastrointestinal stromal cancer. Also, overexpression of mast cells, including, but not limited to, mastocytosis is contemplated. In still another preferred embodiment, the protein kinase related disorder is selected from the group consisting of diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder and a cardiovascular disorder. In yet another preferred embodiment, the organism is a human.

In a eleventh embodiment, the invention relates to a method of treating cancer in companion animals comprising administering a pharmaceutical composition comprising a compound of the first or second embodiments and a pharmaceutically acceptable carrier or excipient. In a preferred embodiment, the companion animal is a cat or a dog.

DETAILED DESCRIPTION OF THE INVENTION

Figure 1:
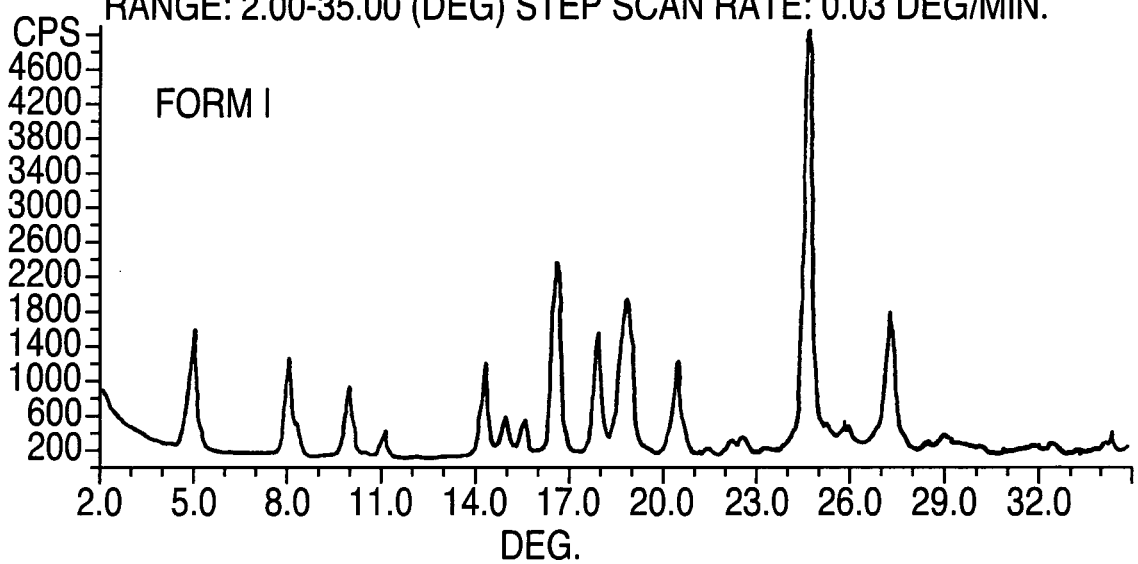
FIG. 1 is a powdered x-ray diffraction (PXRD) pattern for polymorph I (Form I) and polymorph II (Form II) of 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide.
Figure 1:
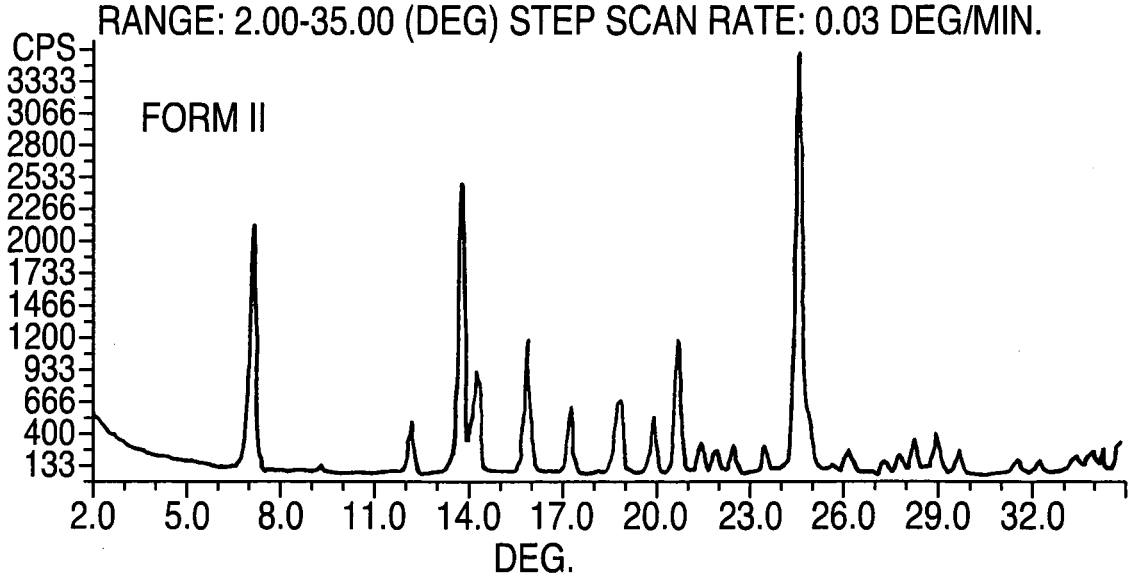

Unless otherwise stated the following terms used in the specification and claims have the meanings discussed below:

"Polymorph" refers to a solid phase of a substance, which occurs in several distinct forms due to different arrangements and/or conformations of the molecules in the crystal lattice.

A polymorph may also be defined as different unsolvated crystal forms of a compound.

Polymorphs typically have different chemical and physical properties. The term "polymorph," in the context of the preferred embodiments of the present invention also includes solvates (i.e., forms containing solvent, or water), amorphous forms (i.e., noncrystalline forms) and desolvated solvates (i.e., forms which can only be made by removing the solvent from a solvate).

In the preferred embodiments of the present invention, pure, single polymorphs as well as mixtures comprising two or more different polymorphs are contemplated. A pure, single polymorph may be substantially free from other polymorphs. "Substantially free" means that other polymorph(s) are present in an amount less than about 15 weight percent, more preferably less than about 10 weight percent, even more preferably less than about 5 weight percent, most preferably less than about 1 weight percent. Someone with ordinary skill in the art would understand the phrase "in an amount less than about 15 weight percent" to mean that the polymorph of interest is present in an amount more than about 85 weight percent. Likewise, the phrase "less than about 10 weight percent" would mean that the polymorph of interest is present in an amount more than about 90 weight percent, and so on and so forth.

Polymorphs of the compounds of the preferred embodiments of the present invention are desirable because a particular polymorph of a compound may have better physical and chemical properties than other polymorphic forms of the same compound. For example, one polymorph may have increased solubility in certain solvents. Such added solubility may facilitate formulation or administration of the compounds of the preferred embodiments of the present invention. Different polymorphs may also have different mechanical properties (e.g., different compressibility, compatibility, tabletability), which may influence tableting performance of the drug, and thus influence formulation of the drug. A particular polymorph may also exhibit different dissolution rate in the same solvent, relative to another polymorph. Different polymorphs may also have different physical (solid-state conversion from metastable polymorph to a more stable polymorph) and chemical (reactivity) stability.

The preferred embodiments of the present invention contemplate a pharmaceutical composition comprising a polymorph of the preferred embodiments of the present invention and a pharmaceutically acceptable carrier or excipient. Carriers and excipients for the formulation of pharmaceutically acceptable compositions comprising the polymorphs of the preferred embodiments of the present invention are well known in the art and are disclosed, for example, in U.S. patent application Ser. No. 09/783,264, filed Feb. 15, 2001, which is incorporated herein in its entirety. See WO 01/60814.

The preferred embodiments of the present invention also contemplate a method for the modulation of the catalytic activity of a protein kinase comprising contacting said protein kinase with a polymorph of the preferred embodiments of the present invention. In a preferred embodiment of the present invention, the protein kinase is selected from the group consisting of a receptor tyrosine kinase, a non-receptor tyrosine kinase and a serine-threonine kinase.

The preferred embodiments of the present invention contemplate a method for treating or preventing a protein kinase related disorder in an organism (e.g., a human) comprising administering a therapeutically effective amount of a pharmaceutical composition comprising a polymorph of the preferred embodiments of the present invention and a pharmaceutically acceptable carrier or excipient to the organism. In a preferred embodiment of the present invention, the protein kinase related disorder is selected from the group consisting of a receptor tyrosine kinase related disorder, a non-receptor tyrosine kinase related disorder and a serine-threonine kinase related disorder. In another preferred embodiment of the present invention, the protein kinase related disorder is selected from the group consisting of an EGFR related disorder, a PDGFR related disorder, an IGFR related disorder and a flk related disorder. In yet another preferred embodiment of the present invention, the protein kinase related disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer. In a preferred embodiment of the present invention, the protein kinase related disorder is selected from the group consisting of diabetes, an autoimmune disorder, a hyperproliferation disorder, restenosis, fibrosis, psoriasis, von Heppel-Lindau disease, osteoarthritis, rheumatoid arthritis, angiogenesis, an inflammatory disorder, an immunological disorder and a cardiovascular disorder.

The preferred embodiments of the present invention also contemplate a method of treating cancer in companion animals comprising administering a pharmaceutical composition comprising a polymorph of the preferred embodiments of the present invention and a pharmaceutically acceptable carrier or excipient. As used herein, the term "companion animal" includes, but is not limited to, cats and dogs.

EXAMPLES

The following examples are given to enable those skilled in the art to more clearly understand and to practice the present invention. They should not be considered as limiting the scope of the invention, but merely as being illustrative and representative thereof.

Synthesis of 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide

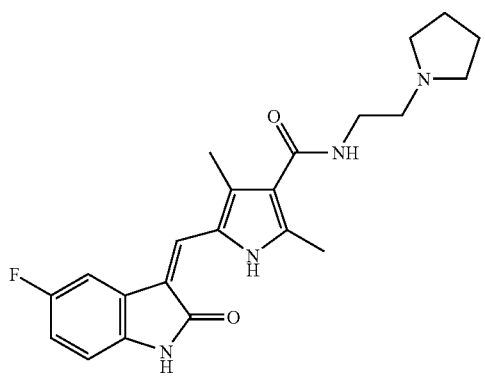

5-Fluoro-1,3-dihydro-indol-2-one was condensed with 5-formyl-2,4-dimethyl-1H-pyrrole-3-carboxylic acid (2-pyrrolidin-1-yl-ethyl)-amide to give the title compound.

MS+ve APCI 397 [M$^+$+1].

Scale-Up Procedure:

5-Formyl-2,4-dimethyl-1H-pyrrole-3-carboxylic acid (61 g), 5-fluoro-1,3-dihydro-indol-2-one (79 g), ethanol (300 mL) and pyrrolidine (32 mL) were refluxed for 4.5 hours. Acetic acid (24 mL) was added to the mixture and refluxing was continued for 30 minutes. The mixture was cooled to room temperature and the solids collected by vacuum filtration and washed twice with ethanol. The solids were stirred for 130 minutes in 40% acetone in water (400 mL) containing 12 N hydrochloric acid (6.5 mL). The solids were collected by vacuum filtration and washed twice with 40% acetone in water. The solids were dried under vacuum to give 5-[5-fluoro-2-oxo-1,2-dihydro-indol-(3Z)-ylidenemethyl]-2,4-dimethyl-1H-pyrrole-3-carboxylic acid (86 g, 79% yield) as an orange solid. $^1$H-NMR (dimethylsulfoxide-d$_6$) δ 2.48, 2.50 (2×s, 6H, 2×CH$_3$), 6.80, 6.88, 7.68, 7.72 (4×m, 4H, aromatic and vinyl), 10.88 (s, 1H, CONH), 12.12 (s, 1H, COOH), 13.82 (s, 1H, pyrrole NH). MS m/z 299 [M−1].

5-[5-Fluoro-2-oxo-1,2-dihydro-indol-(3Z)-ylidenemethyl]-2,4-dimethyl-1H-pyrrole-3-carboxylic acid (100 g) and dimethylformamide (500 mL) were stirred and benzotriazol-1-yloxytris(dimethylamino)phosphonium hexafluorophosphate (221 g), 1-(2-aminoethyl)pyrrolidine (45.6 g) and triethylamine (93 mL) were added. The mixture was stirred for 2 hours at ambient temperature. The solid product was collected by vacuum filtration and washed with ethanol. The solids were slurry-washed by stirring in ethanol (500 mL) for one hour at 64° C. and cooled to room temperature. The solids were collected by vacuum filtration, washed with ethanol, and dried under vacuum to give 5-[5-fluoro-2-oxo-1,2-dihydro-indol-(3Z)-ylidenemethyl]-2,4-dimethyl-1H-pyrrole-3-carboxylic acid (2-pyrrolidin-1-yl-ethyl)-amide (101.5 g, 77% yield). $^1$H-NMR (dimethylsulfoxide-d$_6$) δ 1.60 (m, 4H, 2×CH$_2$), 2.40, 2.44 (2×s, 6H, 2×CH$_3$), 2.50 (m, 4H, 2×CH$_2$), 2.57, 3.35 (2×m, 4H, 2×CH$_2$), 7.53, 7.70, 7.73, 7.76 (4×m, 4H, aromatic and vinyl), 10.88 (s, 1H, CONH), 13.67 (s, 1H, pyrrole NH). MS m/z 396 [M+1].

General Analytical Methods for the Determination of the Identity and Physical Properties of Polymorphs Estimation of the Solubility of a Polymorph in Various Solvents.

Approximately 1.5 mg of the polymorph, was transferred to 10 mL glass vials (tared) and was weighed (accurate to 0.1 mg). Solvents were added to the vials (one solvent each vial) in a step-wise fashion. After each addition, the vial was capped and shaken. The dissolution of solid was visually observed. If no obvious dissolution was observed, more solvent was added immediately. If dissolution was apparent, the vial was left on the bench for at least 30 minutes before the next addition of solvent. This step was repeated until no crystals were visible against a black and a white background. The solubility was then bracketed by dividing the weight by the final volume and the volume before the last addition. If a solid remained after the addition of 10 mL solvent, the solubility was expressed as less than the weight divided by the final volume. If the solid was completely dissolved after the first addition of solvent, the solubility was expressed as greater than the weight divided by the solvent volume. The solubility values were expressed as mg/mL. All experiments were conducted at room temperature.

Determination of the pH—Solubility Profile of Polymorphs.

About 3 mL aqueous solutions of various concentrations of either HCl or NaOH, providing a pH from 1-13, were transferred to a 10 ml glass vial. A sufficient amount of the polymorph was added. The vials were wrapped with aluminum foil and manually shaken. They were allowed to sit in the fume hood overnight prior to any further treatment.

Powder X-ray Diffraction (PXRD).

Powder X-ray diffraction was performed using a Scintag X2 Advanced Diffraction System operating under Scintag DMS/NT 1.30a and Microsoft Windows NT 4.0 software. The system uses a Copper X-ray source (45 kV and 40 mA) to provide CuK$\alpha_1$ emission of 1.5406 Å and a solid-state Peltier cooled detector. The beam aperture was controlled using tube divergence and anti-scatter slits of 2 and 4 mm and detector anti-scatter and receiving slits of 0.5 and 0.2 mm width. Data were collected from 2 to 35 two-theta using a step scan of 0.03/step with a one second per step counting time. Scintag round, top loading stainless steel sample cups with 9 mm diameter inserts were utilized for the experiments. Powders were packed into the holder and were gently pressed by a glass slide to ensure coplanarity between the sample surface and the surface of holders.

Differential Scanning Calorimetry (DSC).

Differential scanning calorimetry (DSC) data were obtained using a DSC calorimeter (TA Instruments 2920). Powder 1-10 mg was packed in an aluminum DSC pan. An aluminum lid was place on top of the pan and was crimped. The crimped pan was placed in the sample cell along with an empty pan as a reference. Temperatures were increased to 300° C. from 30° C. at a rate of 10° C./min.

Polarized Light Microscopy.

Microscopy was conducted on an Olympus BHSP polarized light microscope. Powder was mounted in silicone oil and dispersed between a microscopy slide and a coverslip. Prior to observation, the cover slip was gently rubbed against the slide to render good dispersion of the powder sample. Microscopy was used to assess particle size, shape, and crystallinity of powdered samples. When a hot-stage is affixed to the microscope, thermal events observed by other techniques (e.g., DSC, thermogravimetric analysis (TGA)), may also be visualized.

Fourier-Transformed Infrared Spectroscopy (FTIR).

Polymorph samples were prepared for infrared analysis as KBr pellets. Infrared transmittance data were collected from 4000 to 400 cm−1 on a Nicolet 760 FTIR equipped with a TGS detector. Sensitivity, expressed as instrument gain, was 4. Data were processed as a Fourier transform utilizing a Happ-Genzel apodization. The final FT-IR spectra represented 200 individual scans.

Fourier-Transformed Raman Spectroscopy.

About 2 mg of the polymorph was packed into a 1.7-mm glass capillary tube and was exposed to 1.00 WT 1064-nm laser light. Raman spectra were obtained from 3800 to 100 cm−1. The data were collected using a Nicolet 960 FT-Raman spectrometer equipped with an INGAS detector. Sensitivity, expressed as instrument gain, was 8. Data were again processed as a Fourier transform utilizing a Happ-Genzel apodization. The final FT-Raman spectra represented 200 individual scans.

Rotating Disc Intrinsic Dissolution Rate (IDR) Determination.

The IDR was measured using a fiber optic UV automated dissolution system. The dissolution process was monitored in some instances continuously at 426.2 nm using the fiber optic probe with 10 data points taken per minute. To prepare the compressed disc for the experiment, the powders were compressed in a stainless steel (SS) die, (1¼" diax1", ID 3/16") using a high speed steel (HSS) punch (diameter 3/16" and length 3½"). The HSS punch was inserted into the die to a distance of about ¾", leaving about ¼" for placement of about 10 mg of the drug into the die cavity. A SS base plate (diameter ¼") was placed to cover the cavity. The entire assembly was then secured by a 2-bolt holder. A Carver press was used to compress the powder at to ~1,000 lbs (~37,000 psi) for 3 minutes. The die and holder was removed from the Carver press and the punch was pulled back a little to allow the pellet to relax/expand. The die was then tightly attached on the HSS punch by a set-screw. The entire punch and die assembly containing the drug pellet with one face of the drug pellet exposed was removed as a unit from the holder and was attached to an electric motor. The die was rotated at 300 rpm and was lowered into the dissolution medium 3 min after the initiation of the data collection program. The dissolution medium was degassed and was contained in a 500 mL water jacketed beaker (Pyrex, No.1000). The data collect during the first 3 min provided a baseline value for each dissolution experiment. The dissolution medium consisted of pH=2 solution (0.01 N HCl and 0.05 M KCl). The die was positioned such that the drug compact was about 2.5" from the bottom of the 500 mL dissolution vessel and about the same distance from the liquid surface.

The intrinsic dissolution profile was plotted using Microsoft Excel and the intrinsic dissolution rate was calculated automatically by the program according to equation (1).

$$IDR\ (mg \cdot cm^{-2} min^{-1}) = \frac{Slope\ (mg \cdot mL^{-1} min^{-1}) \cdot 300\ mL}{0.177\ cm^2} \quad (1)$$

The volume of dissolution medium was 300 mL. The surface area of the pellet exposed to dissolution medium was 0.177 cm². The time period for a dissolution run was usually 15 min but was varied as needed.

Determination of the Physical Properties of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide Polymorphs Two polymorphic forms of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide were identified. The thermodynamic relationship between the two polymorphic forms of the compound, their dissolution behavior, and their solid-state properties became immediately apparent for solid form selection and for proper process control during active pharmaceutical ingredient (API) manufacture. Therefore, an effort was made to understand the stability relationship between the two polymorphic forms of the compound and to characterize their solid-state properties using a variety of techniques (e.g., solubility, IDR, PXRD, IR/Raman spectroscopy, polarized light microscopy and DSC).

Solubility

The estimated solubilities of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide in various solvents are presented in Table A. The experiments were carried out using polymorph I at room temperature. The solubilities may be divided into three groups.

Group I

Solubility of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide in isopropyl alcohol, $CH_2Cl_2$, ethyl acetate, acetonitrile, acetone, chloroform, toluene, hexane and water pH>6 water: the solubility is very low (<<0.3 mg/mL).

Group II

Solubility in methanol, ethanol, dioxane and THF: the solubility is still low (0.1-0.4 mg/mL), but appears significantly higher than solubilities in solvents of Group I.

Group III

Solubilities of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide in dimethylsulfoxide (DMSO), dimethylformamide (DMF), and pH<=2 water: the solubility is relatively high (>1 mg/mL).

TABLE A

Estimated solubility of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide polymorph I in various solvents at 23° C.

| | Solvent | Solubility (mg/mL) |
| --- | --- | --- |
| 1 | Water (pH = 2) | 3.11 |
|   | Water (pH = 6) | 0.005 |
| 2 | DMSO | 1.5-3.0 |
| 3 | DMF | >1.5 |
| 4 | methanol | 0.21-0.31 |
| 5 | ethanol | 0.17-0.19 |
| 6 | Dioxane | 0.18-0.20 |
| 7 | THF | 0.32-0.4 |
| 8 | Isopropanol | <0.14 |
| 9 | $CH_2Cl_2$ | <0.12 |
| 10 | Ethyl acetate | <<0.28 |
| 11 | Acetonitrile | <<0.08 |
| 12 | Acetone | <<0.16 |
| 13 | Chloroform | <0.11 |
| 14 | Toluene | <<0.13 |
| 15 | Hexane | <<<0.13 |
| 16 | PEG 400 | 0.30-0.43 |

The pKa of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide is 8.50. As expected, the equilibrium solubility of this compound is higher at lower solution pH (Table A). However, the dissolution of a particle in a dissolution medium depends on the pH in the diffusion layer. The pH value of the diffusion layer in intimate contact with the solid ($pH_{h=0}$) may be obtained from equilibrium pH of the solution, measured by a pH meter. Results are presented in Table B. When the initial pH is higher than 10, the solubility of 5-[5-fluoro-2-oxo-1,2-dihydroindol-(3Z)-ylidenmethyl]-2,4-dimethyl-1 H-pyrrole-3-carboxylic acid (2-pyrrolidin-1-ylethyl)-amide is very low. Therefore, the pH of the solution at equilibrium is almost not changed. On the other hand, if the initial pH<10, more 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide goes into solution and the equilibrium solution pH is higher than the initial pH (Table B). Therefore, the data suggest that $pH_{h=0}$ is maintained relatively high (>5), even when the bulk dissolution medium has a pH as low as 1.4.

TABLE B

Effect of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide on equilibrium solution pH values of non-buffered aqueous medium at ambient temperature.

| Initial solution pH | Amount of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide added to 2 mL non-buffered water (mg) | Equilibrium solution pH |
| --- | --- | --- |
| 1.43 | 322.5 | 5.36 |
| 2.19 | 333.2 | 5.20 |
| 3.22 | 280.7 | 6.98 |
| 5.47 | 209.7 | 8.13 |
| 6.73 | 143.0 | 8.31 |
| 7.24 | 141.5 | 8.49 |
| 7.61 | 95.4 | 8.87 |
| 10.07 | 95.1 | 9.86 |
| 11.53 | 96.2 | 11.61 |
| 12.50 | 88.0 | 12.52 |
| 13.20 | 98 | 13.18 |

An attempt to measure the pH—solubility profile of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide was not successful. Very fine particles were formed upon dissolution of the initial drug in pH<2.2. Those fine particles went through a 0.45 μm filter membrane and yielded a cloudy filtrate. A filter membrane with smaller pore (0.1 μm) was not tried because no immediate use of such data is apparent.

IDR

The intrinsic dissolution rate (IDR) of polymorph II was compared to that of polymorph I. It was found that the IDR of polymorph II is about three times of apparent IDR of polymorph I in pH 2 buffer at 23° C. (Table C). This result contradicts the earlier observation that polymorph II is less stable and expected to have a lower solubility and therefore, lower IDR at the same temperature and in the same solvent. While not wishing to be bound by theory, one explanation to the contradiction is that the drug undergoes solid-state conversion at the experimental conditions. Consequently, IDR can not be compared with the thermodynamic relationship of the original two polymorphs. Microscopic observation of the drug pellet of polymorph I showed positive evidence for the solid-state conversion hypothesis. The color of the pellet on the side exposed to the dissolution medium was orange-red comparing to the yellow color of the original pellet. It is possible that polymorph I had converted to HCl salt as soon as the pellet was in contact with the dissolution medium (0.05M KCl, pH 2 buffer). Due to a common ion effect, the solubility and therefore the IDR of the newly formed HCl salt is much lower than would have been expected for polymorph II. No obvious color change was observed after the polymorph II pellet was exposed to the same dissolution medium.

To further test the HCl salt formation hypothesis. Both polymorph I and II were suspended in the above dissolution medium. However, no change of color of the particles was observed at least 15 minutes after the suspension was made. This result agrees with the observed solid-state stability of polymorph II during the course of the dissolution experiment, but does not support the rapid conversion of polymorph I pellet to a HCl salt. One day after the suspensions were prepared, orange-red needle-shaped crystals, presumably HCl salt crystals, appeared in both vials. This result confirms that the solubility of HCl salt is lower than the solubilities of both polymorph I and II in the medium used for dissolution tests. It is also possible that compaction prior to the IDR experiment modify the crystals of polymorph I and render it the ability of rapid conversion. The XRD pattern of polymorph I pellets compressed at various pressures show some degree of amorphous content, which may be connected to its rapid salt formation during the IDR experiment.

Powder X-Ray Diffraction (PXRD)

Distinctively different powder X-ray diffraction (PXRD) patterns of two batches of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide were observed (FIG. 1). Such an observation suggests the existence of polymorphism of this drug. Therefore FTIR and Raman spectroscopy were used to confirm the polymorphism of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide.

IR and RAMAN Spectroscopy

Figure 2:
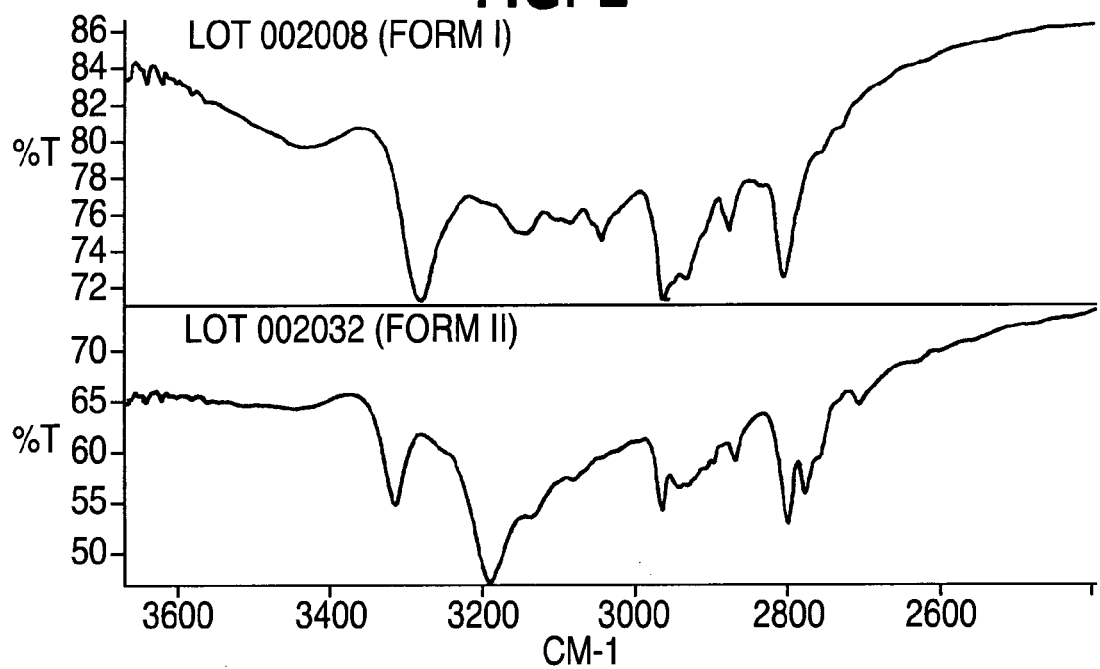
FIG. 2 are infra red (IR) transmittance spectra, measured at the high and mid-frequency regions of the IR spectrum, for polymorph I (top spectra) and polymorph II (bottom spectra) of 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide.
Figure 2:
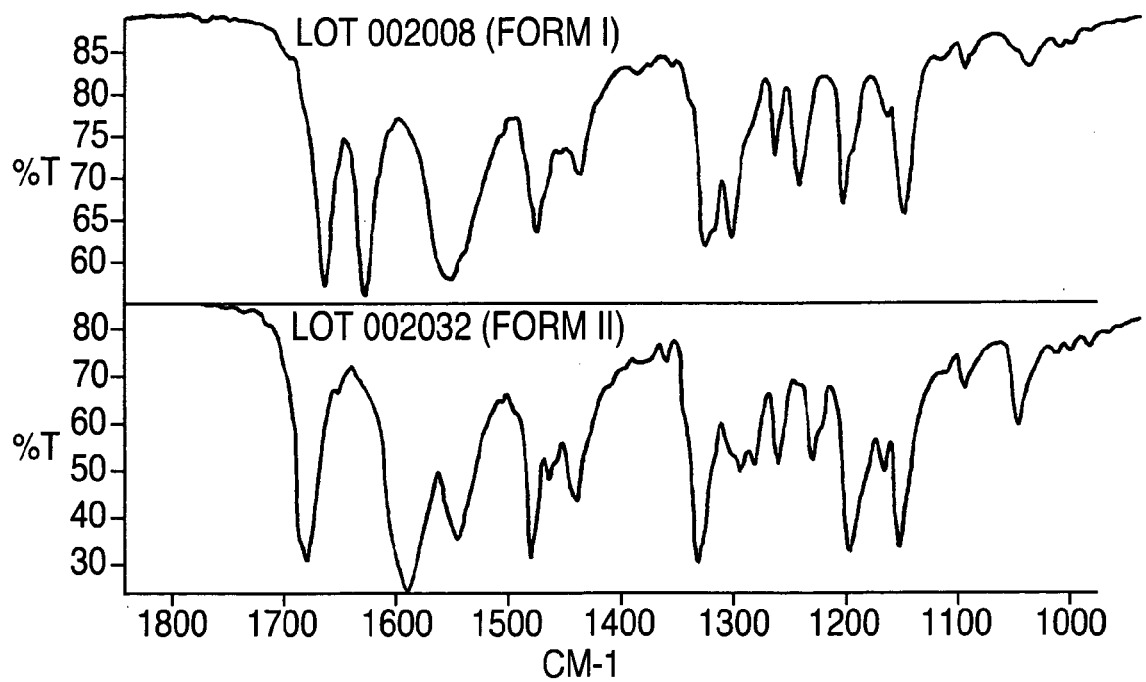
Figure 3:
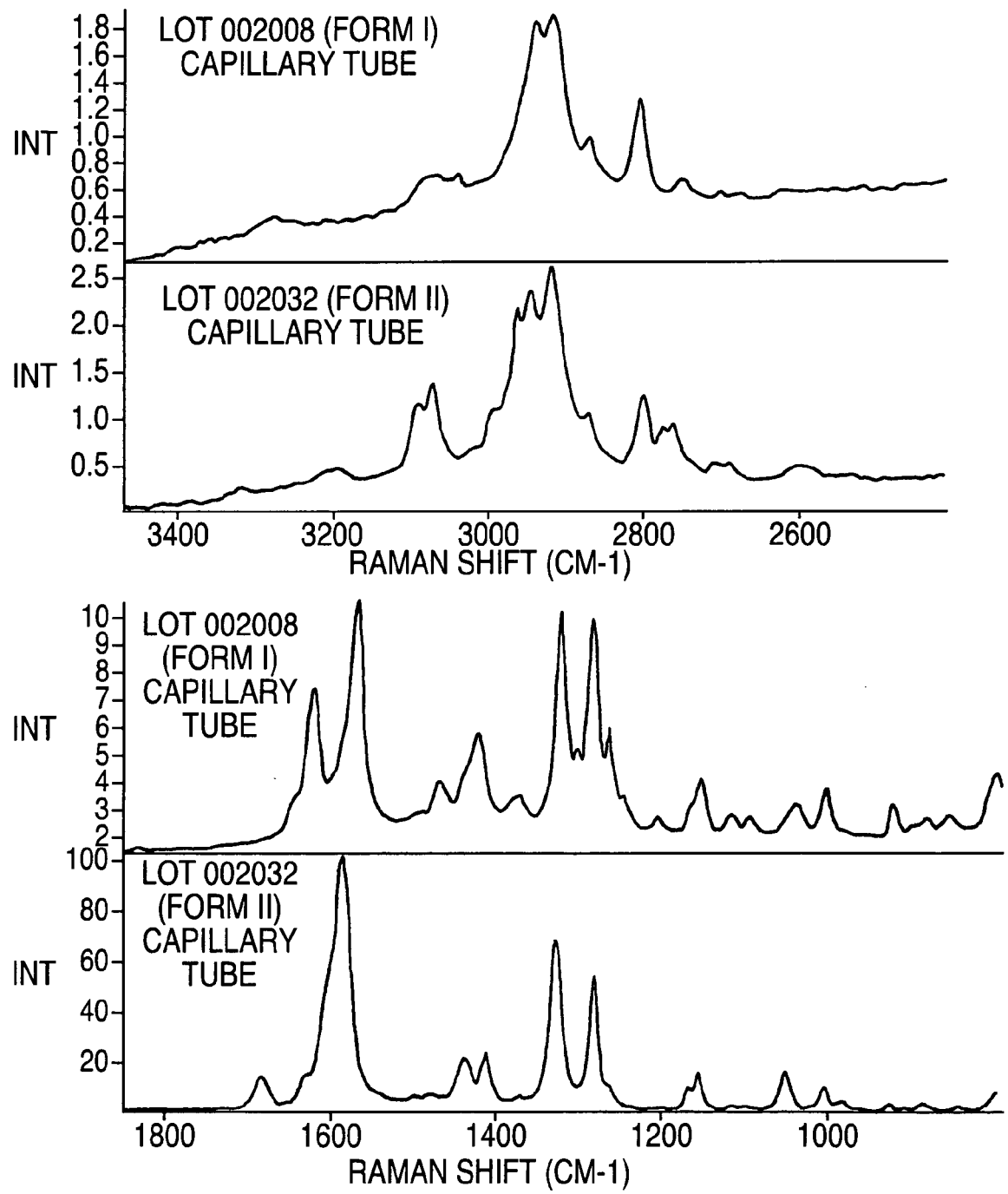
FIG. 3 is a Raman spectrum, measured at the high and mid-frequency regions of the Raman spectrum, for polymorph I (top spectra) and polymorph II (bottom spectra) of 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide.

IR and Raman spectra are shown in FIGS. 2 and 3, respectively. Spectral variations are clearly observed in the data for the two Forms of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide. In general, these variations involve changes in the vibrational modes associated to the N—H and C=O functional groups of the molecules. There are also some changes observed in the C—H stretching modes of the two forms. Solution NMR data (in DMSO) of polymorphs I and II of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide were identical confirming that both polymorphic forms of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide are chemically equivalent. Therefore, any vibrational spectral differences between the two samples is likely due to crystal packing of the two forms of 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide.

An inspection of the IR data for polymorph II shows the appearance of a broad vibrational band at 3198 $cm^{-1}$ that is not present in the spectra of polymorph I. Broad vibrational bands at this frequency can be due to O—H stretching. The IR data for polymorph II also lack the C=O amide carbonyl stretch that is found in the polymorph I spectra at 1631 $cm^{-1}$. Conversely, the IR data for polymorph II exhibit a strong peak at 1589 $cm^{-1}$ that is not present in the data for polymorph I. A vibration at this frequency is typical of C=N stretching. The presence of C=N and O—H stretching modes, coupled with the loss of a C=O vibration in the IR data for polymorph II, compared to the analogous data for polymorph I, suggest keto-enol tautomeric differences between the two forms. The location of this change among the three amide carbonyl groups is not known. However, the splitting of the $CH_2$ vibration in the IR data for polymorph I at 2798 $cm^{-1}$ into two vibrational bands at 2798 and 2776 $cm^{-1}$ in polymorph II data suggest that the enolization may take place at the amide moiety adjacent to the methylene group, possibly facilitated by a rotation about the C—N amide bond. The FTIR spectra of both polymorphs were shown in FIG. 2. The Raman spectra are (FIG. 3) also show similar differences between powders of the two polymorphs.

Polarized Light Microscopy

Both polymorphs show birefriengence under polarized light microscope. Therefore, both polymorphs are crystalline, agreeing with the strong diffraction peaks in PXRD patterns. The particles in polymorph I are much smaller than those in polymorph II.

Thermodynamic Stability

Differential Scanning Calorimetry (DSC)

DSC scans of both polymorphs show different melting point and different enthalpy of melting (Table C). The melting point of polymorph II is about 3° C. higher than that of polymorph I. Therefore, polymorph II is the thermodynamically more stable polymorph near melting temperature. The higher melting point polymorph II also has a higher enthalpy of melting. Therefore, the "Heat of fusion" rule predicts that the two solid Forms are monotropicly related. Melting points observed by hot stage microscopy show similar difference (about 3° C.). From both DSC and hot-stage microscopy, no heat event was observed at temperature below the melting temperature of each polymorph.

TABLE C

Melting points ($T_m$), enthalpy of fusion ($H_f$), and intrinsic dissolution rates (IDR) of two polymorphs.

| Physical properties | polymorph I | polymorph II |
|---|---|---|
| $T_m$ (° C.)[a] | 256.3 | 259.4 |
| $H_f$ (J/g)[a] | 55.78 | 85.44 |
| IDR (n = 3)[b] (mg/min/$cm^2$) | 1.08 ± 0.09[c] | 3.54 ± 0.15 |

[a]Melting temperature and enthalpy of fusion was measured by DSC. The melting point is taken as the onset temperature.
[b]pH = 2 buffer (0.01 N HCl and 0.05 M KCl) at 23° C.
[c]Polymorph I undergoes solution mediated phase conversion. The measured IDR value does not represent the true IDR of the polymorph I.

PXRD

To determine the relative thermodynamic stability relationship between two polymorphs, a slurry conversion experiment was also studied at room temperature using PXRD. The results are shown in Table D.

The skilled artisan would recognize that the thermodynamic stability of the polymorph in question will depend upon a number of factors, including, but not limited to, sample size, stirring rate (if the sample is stirred), whether a seed crystal is utilized, the relative ratio between the polymorphs present, the solvent used and the temperature.

TABLE D

Suspension crystallization conditions and polymorphic nature of resulting solids as identified by PXRD.

| Solvent | Initial solid[a] | Resulting solid by PXRD |
|---|---|---|
| Methanol | I + seeds of II | II |
| Ethanol | I + seeds of II | $ND^b$ |
| Acetonitrile | I + seeds of II | $ND^b$ |
| Acetone | I + seeds of II | II |
| THF | I + seeds of II | I |
| DMSO + H2O (1:1, v:v) | I + seeds of II | $ND^b$ |
| Methanol | I + II (2:1, w/w) | II |

[a]Polymorph I used here is the lot 2008. Polymorph II used here is 35282-CS-11.
[b]Most of the solid went through filter paper. No sufficient material was collected for PXRD analysis.

Polymorph I, 20 mg, was suspended in various solvents alone with trace amount of polymorph II seeding crystals in 10 mL glass vials. The suspensions were stirred by magnetic stirring bars for 2 weeks before the solids were filtered and analyzed by PXRD. Results show that methanol and acetone suspensions yield pure polymorph II, i.e., polymorph I converts to polymorph II mediated by the two solvents. Therefore, the data suggest that polymorph II is thermodynamically more stable than polymorph I at room temperature. Because polymorph II is also more stable near the melting temperature, the two polymorphs are monotropically related, i.e., polymorph II is more stable from room temperature to melting temperature. However, polymorph I appears stable in tetrahydrofuran (THF) suspension. Because the solubility in THF is higher than that in acetone (Table A), low solubility is not the reason for the slow conversion kinetics.

While not wishing to be bound by theory, it is possible that THF molecules interact uniquely with 5-[5-fluoro-2-oxo-1,2-dihydroindol-(3Z)-ylidenmethyl]-2,4-dimethyl-1H-pyrrole-3-carboxylic acid (2-pyrrolidin-1-ylethyl)-amide molecules in solution and inhibit the nucleation and crystal growth of polymorph II and subsequently cause polymorph I kinetically stable in THF.

The following describes the preparation of polymorphs I and II.

Preparation of Polymorph I: Method 1

24.8 mg of 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide was completely dissolved by adequate amount (at least 6 mL) of pH2 buffer (0.01 N HCl and 0.04 M KCl) while heated on a hot-plate. The solution was cooled in a fume-hood for 5 min. Solution of 1 N NaOH was added to induce precipitation from the solution. The solid was free of polymorph II and was constituted of mainly polymorph I with some amorphous characteristics.

Preparation of Polymorph I: Method 2

41.3 mg 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide was mixed with 25 mL tetrahydrofuran (THF) and 5 mL water. The mixture was heated slightly to dissolve the solid. The resulted clear solution was collected into an uncapped glass vial to allow evaporation of the solvent. Precipitation occurs when adequate amount of solvent evaporate. The precipitate was constituted of needle-shaped crystals as shown by microscopic observation. The precipitate was filtered out and was gently ground before being analyzed by XRD. The grinding reduce the particle size of the solid obtained and reduced effect of preferred orientation of crystals on PXRD patterns. PXRD results showed that the solid is pure polymorph I.

Preparation of Polymorph II

About 6 mg 5-(5-fluoro-2-oxo-1,2-dihydro-indol-3-ylidenemethyl)-2,4-dimethyl-1H-pyrrole-3-carboxylic acid (2-pyrrolidin-1-yl-ethyl)-amide was dissolved in at least 20 mL of methanol to provide a clear solution. Slight heating may be appropriate to facilitate the dissolution of solid. This methanol solution was cooled and slowly evaporated to dryness in an ambient environment. Small amount of methanol (~2 mL) was then added to dissolve part of the solid. The remaining crystals were polymorph II.

From the foregoing description, one skilled in the art can easily ascertain the essential characteristics of this invention, and without departing from the spirit and scope thereof, can make various changes and modifications of the invention to adapt it to various usages and conditions without undue experimentation.

What is claimed is:

1. A polymorph form (polymorph II) of a compound of formula I:

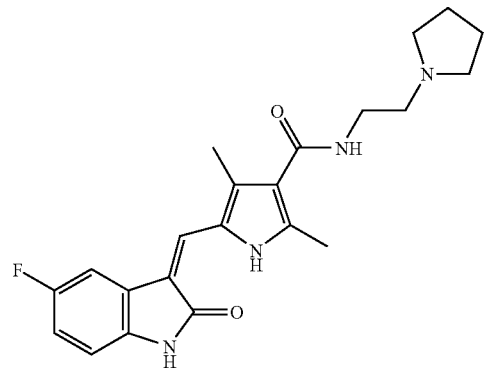

wherein the polymorph form has a powder X-ray diffraction spectrum comprising peaks expressed in degrees (±0.1 degree) of two theta angle of 7.1, 13.9, 16.0, 20.9, and 24.7 obtained using CuK$\alpha_1$ emission (wavelength=1.5406 Angstroms).

2. A polymorph form (polymorph I) of a compound of formula I:

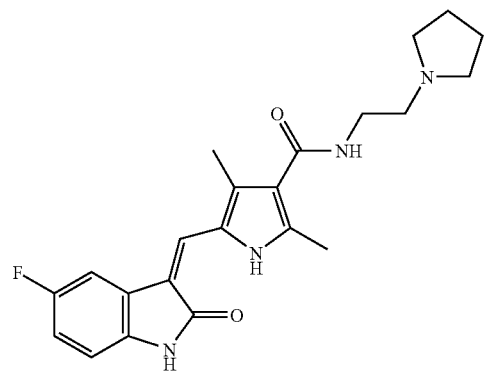

wherein the polymorph form has a powder X-ray diffraction spectrum comprising peaks expressed in degrees (±0.1 degree) of two theta angle of 5.0, 16.7, 18.9, 24.8, and 27.3 obtained using CuKu$\alpha_1$ emission (wavelength=1.5406 Angstroms).

3. A solid composition comprising the polymorph of claim 2, wherein said polymorph comprises at least 85 weight percent of the composition.

4. The composition of claim 3, wherein said polymorph comprises at least 90 weight percent of the composition.

5. The composition of claim 3, wherein said polymorph comprises at least 95 weight percent of the composition.

6. The composition of claim 3, wherein said polymorph comprises at least 99 weight percent of the composition.

7. A solid composition comprising the polymorph of claim 1, wherein said polymorph comprises at least 85 weight percent of the composition.

8. The composition of claim 7, wherein said polymorph comprises at least 90 weight percent of the composition.

9. The composition of claim 7, wherein said polymorph comprises at least 95 weight percent of the composition.

10. The composition of claim 7, wherein said polymorph comprises at least 99 weight percent of the composition.

11. a process for preparing the polymorph of claim 2, wherein said polymorph is made by:
 (a) dissolving said compound of claim 2 in an acidic aqueous solution;
 (b) basifying said aqueous solution thereby precipitating the polymorph I form; and
 (c) isolating the precipitated polymorph I form of said compound.

12. A process for preparing the polymorph of claim 2, wherein said polymorph is made by:
 (a) dissolving said compound of claim 2 in a polar organic solvent that does not form hydrogen bonds;
 (b) evaporating said polar organic solvent thereby precipitating the polymorph I form; and
 (c) isolating the precipitated polymorph I form of said compound.

13. A process for preparing the polymorph of claim 1, wherein said polymorph is made by:
 (a) dissolving said compound of claim 1 in a polar organic solvent that forms hydrogen bonds;
 (b) evaporating said polar organic solvent thereby precipitating the polymorph II form; and
 (c) isolating the precipitated polymorph II form of said compound.

14. The process of claim 12, wherein said polar organic solvent that does not form hydrogen bonds is THF.

15. The process of claim 13, wherein said polar organic solvent that forms hydrogen bonds is methanol.

16. A pharmaceutical composition, comprising a polymorph form of one of claims 1 or 2 and a pharmaceutically acceptable carrier or excipient.

* * * * *

UNITED STATES PATENT AND TRADEMARK OFFICE
CERTIFICATE OF CORRECTION

| | | |
|---|---|---|
| PATENT NO. | : 7,452,913 B2 | Page 1 of 1 |
| APPLICATION NO. | : 10/776337 | |
| DATED | : November 18, 2008 | |
| INVENTOR(S) | : Sun et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1051 days.

Signed and Sealed this
Seventeenth Day of April, 2012

David J. Kappos
*Director of the United States Patent and Trademark Office*